United States Patent [19]

Walter

[11] 4,273,868
[45] Jun. 16, 1981

[54] COLOR STABLE GLUCOSE TEST

[75] Inventor: Bert Walter, South Bend, Ind.

[73] Assignee: Miles Laboratories, Inc., Elkhart, Ind.

[21] Appl. No.: 14,500

[22] Filed: Feb. 23, 1979

[51] Int. Cl.³ .............................................. C12Q 1/54
[52] U.S. Cl. .......................................... 435/14; 435/28
[58] Field of Search ............................. 435/14, 28, 25

[56] References Cited

U.S. PATENT DOCUMENTS

| 2,905,594 | 9/1959 | Morris | 435/28 |
| 3,350,278 | 10/1967 | Gretton et al. | 435/14 |
| 3,853,470 | 12/1974 | Morin et al. | 435/14 X |

FOREIGN PATENT DOCUMENTS 1464359 2/1977 United Kingdom .
1464360 2/1977 United Kingdom .

Primary Examiner—Thomas G. Wyse
Attorney, Agent, or Firm—Charles J. Herron

[57] ABSTRACT

Test means, such as a composition, a test device, method of making the test device and process for determining glucose in a body fluid sample are disclosed. More particularly, the contemplated test means comprises glucose oxidase, a peroxidatively active substance, such as peroxidase, and a 3,3',5,5'-tetraalkylbenzidine indicator in an amount sufficient rapidly to produce upon contact of the test means with a predetermined amount of a glucose containing sample, a stable colored reaction product. The preferred benzidine indicator is 3,3',5,5'-tetramethylbenzidine.

1 Claim, 5 Drawing Figures

COLOR STABLE GLUCOSE TEST

FIELD OF THE INVENTION

The present invention relates generally to the field of diagnostic tests and, more particularly, to those tests useful in qualitative and quantitative determination of glucose in which tests glucose is converted to a peroxide.

BACKGROUND OF THE INVENTION

Glucose oxidase enzymatically converts glucose to gluconic acid and hydrogen peroxide. The hydrogen peroxide thus formed can be reduced to $H_2O$ by a peroxidatively active substance in the presence of an indicator system which is oxidized to produce a response, such as a color change. The chromogenic indicator o-tolidine has been used for some time in glucose test systems, but provides results which are subject to reduction of the oxidized indicator by interfering substances, such as ascorbic acid. Further, the safety of o-tolidine has been questioned.

British published Pat. Nos. 1,464,359 and 1,464,360 which disclose the use of 3,3',5,5' tetramethylbenzidine and similar compounds and their use in the detection and determination of hydrogen peroxide or of constituents which react to form peroxides. Concentrations of the benzidine derivatives disclosed therein are inconsistent and are generally not more than about 6 milligrams/milliliter of impregnating solution used.

The use of the benzidine derivatives at the concentrations disclosed in the aforementioned British published specifications results in relatively slow formation of a color or formation of a color that does not remain stable over a period of time. In the latter case, the developed color tends to deteriorate upon standing, making readings susceptible to error and difficult or impossible by untrained personnel.

OBJECTS OF THE INVENTION

It is therefore an object of the present invention to provide an improved test for the detection of glucose.

It is yet another object of the invention to provide an improved test for glucose using materials which are recognized for their safety.

A further object of the invention is to provide an improved test for the detection of glucose which forms a color that remains stable over time.

A still further object of the invention is to provide an improved test for the detection of glucose in a sample wherein the above-identified advantages are achieved through a novel test means comprising glucose oxidase, a peroxidatively active substance and a 3,3',5,5'-tetraalkylbenzidine indicator, the latter being present in an amount sufficient rapidly to produce, upon contact of the test means with a predetermined amount of a glucose-containing sample, a stable colored reaction product.

BRIEF DESCRIPTION OF THE DRAWINGS

Other objects and a fuller understanding of the invention will be had by referring to the following description and claims drawn to preferred embodiments thereof, taken in conjunction with the accompanying drawings in which:

SUMMARY OF THE INVENTION

Figure 1:
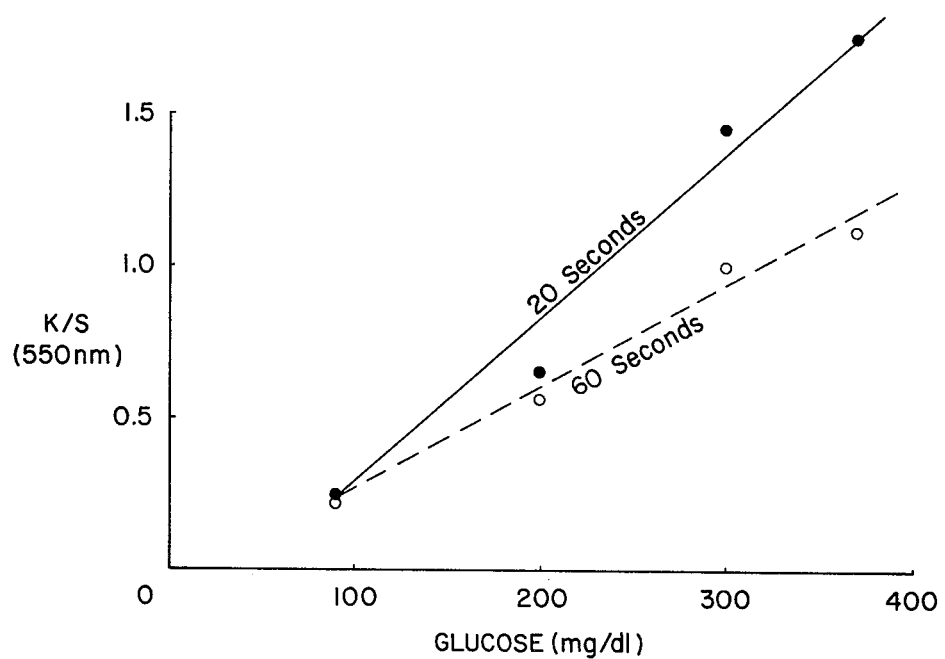
FIG. 1 is a graphical representation of the data reported in Table I using glucose test devices produced with the use of impregnating solution formula I of Example I, such representation being obtained by plotting K/S, defined infra, vs glucose concentration.

In contrast to prior art compositions, those of the present invention are substantially free from the problem of color deterioration. This unexpected property is observed upon increasing the concentration of the 3,3',5,5'-tetraalkylbenzidine indicator. The invention therefore differs from present methology in that it rapidly provides a color which remains stable following its formation. One does not have to wait for the indicator color to stabilize nor be concerned with a continuous change in color during the time after initiation of color formation. According to the invention a composition and device are now available using a 3,3',5,5'-tetraalkylbenzidine rapidly to produce a stable color upon contact thereof with the sample containing glucose in the range of from a small but detectable amount up to at least about 400 milligrams/deciliter.

In accordance with the present invention there are provided test means, such as a composition, a test device, method of making the test device and process for determining glucose in a sample. More particularly, the contemplated test means comprises glucose oxidase, a peroxidatively active substance, such as peroxidase, and a 3,3',5,5'-tetraalkylbenzidine indicator in an amount sufficient rapidly to produce, upon contact of the test means with a predetermined amount of a glucose-containing sample, a stable colored reaction product believed to comprise reduced and oxidized forms of said indicator in stable equilibrium. The stable colored reaction product is produced within a time period of not more than about 60 seconds and, more specifically, between about 30 and 60 seconds after contact of the test means with the body fluid sample to be tested.

The concentration of 3,3',5,5'-tetraalkylbenzidine in relationship to the amount of glucose oxidase activity present in the test means of the invention is critical. In accordance with the invention the 3,3',5,5'-tetraalkylbenzidine is present in the test means in a concentration of at least about 2.5 millimoles (mM) per thousand International Units (I.U.) of glucose oxidase activity.

The 3,3',5,5'-tetraalkylbenzidine compounds are particularly advantageous as they have been recognized for their noncarcinogenic properties.

Likewise, there is provided a test device for the determination of glucose, which device comprises a carrier or matrix incorporated with the test means of the invention. A test device can take the form of a tablet or, preferably, a device of the test strip form. Elongated sheets of carrier material which have been incorporated with the test means of the invention are contemplated as devices as used herein. In manufacture and distribution these elongated sheets may take the form of bulk rolls, such as of filter paper material. The device is prepared, for example, by impregnating a carrier with a solution of the test means of the invention and thereafter drying the impregnated carrier. A process for the determination of glucose in a fluid sample is provided which comprises contacting a sample with the test means or device according to the invention and observing any resultant color change.

DESCRIPTION OF THE PREFERRED EMBODIMENTS

Although specific terms are used in the following description for the sake of clarity, these terms are intended to refer only to the particular embodiment of the invention selected for exemplary illustration, and are not intended to define or limit the scope of the invention.

The test means according to the invention can take many physical forms and include many specific 3,3',5,5'-tetraalklbenzidines regardless of the form assumed. These, along with know additives such as stabilizing agents, which can additionally be employed if desired, are described. The test means is used to detect glucose by contacting it with a specimen such as urine, blood, serum, cerbrospinal fluid, tissue culture supernatant or the like.

The various benzidine indicators which can be used include the 3,3',5,5'-tetraalkylbenzidines, wherein alkyl is a $C_1$–$C_4$ alkyl, and 3,3',5,5'-tetramethylbenzidine is particularly preferred. Others which can also be used include 3-methyl, 3'-methyl, 5-ethyl, 5'-ethyl benzidine and 3,3', 5,5'-tetraethylbenzidine. As can be seen from these samples, the four alkyl groups can be the same or different.

Glucose enzymes which can be used are those which will react with a glucose-containing fluid being tested to produce a predetermined reaction product, such as hydrogen peroxide. For example, glucose oxidase obtained from molds can be used. These are usually referred to as the flavo-protein type since they contain as a prosthetic group or coenzyme a flavin or isoalloxazine.

Preferably, a dual enzyme system is present: one enzyme transforms glucose to produce hydrogen peroxide, whereas the other enzyme has peroxidative activity. Substances having peroxidative activity which are useful in the present invention can be chosen from various organic and inorganic sources. Plant peroxidases, such as horseradish peroxidase or potato peroxidase, can be used. Inorganic compounds having peroxidase activity include iodides, such as sodium and ammonium iodides, and molybdates, such as potassium and ammonium molybdates. In addition, urohemin and a number of other porphyrin substances having peroxidative activity can be used. Other substances which are not enzymes, but which have peroxidative activity include such compounds as iron sulfocyanate, iron tannate, ferrous ferrocyanide, potassium chromic sulfate and the like.

Since the compositions employed to measure glucose in blood, for example, should be maintained at a pH level in the range of from about pH4 to about pH 7.5, a buffer system comprising tris(hydroxymethyl)aminomethane, malonic acid and disodium malonate is particularly useful for this purpose.

An interpolymer of methylvinyl ether and maleic anhydride is also useful in the formulation of glucose indicators of the present invention. One such interpolymer is marketed commercially as Gantrez AN-139 by GAF Corporation. When this interpolymer is dissolved in an alcohol it forms a partial ester derivative, and when the interpolymer is dissolved in water it forms an acid derivative. Since test means prepared in accordance with the present invention are typically prepared from aqueous alcohol solutions, test compositions in the final product will contain either an acid derivative or a partial ester derivative or a mixture of said derivatives. The presence of the above described interpolymer derivatives along with polyvinyl pyrrolidone (PVP) having, for example, an average molecular weight of about 40,000, greatly enhances the color formed when color forming indicators are oxidized by hydrogen peroxide in the presence of peroxidase. This enhancement of color aids in more sharply defining different color shades for different levels of glucose content in a given fluid sample. This is particularly important to the physician in his diagnosis of the presence of an incipient diabetic condition.

Also provided are test devices incorporating the test means of the invention and a method of making such test devices which comprising incorporating a carrier with the test means. In addition to impregnation as aforedescribed, incorporation of the carrier with the test means can be effected by other suitable techniques, such as by printing or spraying the test composition onto the carrier.

Preferably the test device is prepared by a process which comprises impregnating a carrier with a first solution having from about $4 \times 10^4$ to about $8 \times 10^4$ International Units of glucose oxidase activity and about $22 \times 10^5$ International Units of peroxidase activity per liter and, after drying said carrier with a second solution having at least about 6 grams of 3,3'5,5'-tetraalkylbenzidine per liter for each about $1 \times 10^4$ International Units of glucose oxidase activity per liter in said first solution. The impregnated carrier is again dried after the second impregnation.

The term carrier refers to matrices which are insoluble in and maintain their structural integrity when exposed to physiological or other liquid to be tested. Suitable matrices which may be used include paper, cellulose, wood, synthetic resin fleeces, glass fiber, nonwoven and woven fabrics, gelatin, various organic polymers, such as polypropylene, and other organic materials well known as film formers to those skilled in the art. Alternatively, the carrier may take the form of a pressed or molded tablet containing conventional carrier material. For convenience, the carrier can be suitably attached to an insoluble support or handle member which can be made from polystyrene.

When the test composition is to be used for detecting glucose in blood, the surface of the impregnated carrier matrix is advantageously covered with a semipermeable transparent coating or film of ethyl cellulose or other suitable material. This can be accomplished by applying a layer of ethyl cellulose dissolved in benzene, for example, to the surface of the impregnated carrier matrix and then removing the solvent by evaporating drying. Alternatively, the ethyl cellulose can be part of the second impregnating solution as in the example.

Glucose test devices in the form of treated carrier matrices are often stored for considerable periods of time before use, and it is therefore desirable that the reagents chosen are not easily auto-oxidizable in air. Advisably, the test devices should be protected from exposure to light and in some cases it is desirable to keep them sealed in a moisture repellent package which is opened only for removal of one or more test devices shortly before use.

If desirable, a carrier matrix can be treated with a background dye of a particular color, such as yellow, so that the color produced by reaction with glucose is blended with the background color to produce varying tints which correspond to the concentration of glucose present in the fluid or liquid being tested. It may be especially desirable to dye the matrix yellow when the colored reaction product is blue.

The test device is advantageously used by momentarily dipping it in a test sample or by otherwise introducing a test sample into the carrier matrix, whereby a detectable color change results when glucose is present. The volumetric capacity of the carrier serves to limit the amount of sample absorbed thereby and to which the test means incorporated therewith is exposed. Any excess sample can be removed by washing or blotting the carrier to thereby limit the amount of sample tested to the volume thereof which has actually entered the carrier matrix. The test device can be used in the same way when samples of plasma, serum or other body fluids are tested.

Reflectance readings of color produced by reaction with glucose present in sample can be obtained from commerically available spectrophotometers such as Beckman DK-2 Spectrophotometer, Beckman Instruments, Inc., Fullerton, Calif. or Spectrocolorimeter SCF-1, Israel Electro-Optical Industry Ltd. (distributed in the U.S. by Broomer Research Corporation, Plainwell, Long Island, N.Y.).

For highly precise determinations of glucose concentration, photoelectric, colorimetric or spectrophotometric methods can be employed to determine color indication. The EYETONE ® reflectance colorimeter (Ames Company, Division of Miles Laboratories, Inc.) is a portable instrument designed to quantitatively measure whole blood glucose when used in conjunction with DEXTROSTIX ® reagent strips (Ames Company, Division of Miles Laboratories, Inc.). The EYETONE reflectance colorimeter measures the light reflected from the surface of the reacted test device matrix and converts this measurement, by means of electronic circuitry, to a reading on a precisely calibrated meter scale on the instrument which is capable of indicating blood glucose within the range of 10 to 400 milligrams (mg)/100 milliliter (ml). The higher the blood glucose level, the darker the strip and the less light reflected. Conversely, the lower the blood glucose level the lighter the strip and the more light reflected. The colorforming test means or device described herein has been found to be especially useful in that it provides a unique color response which can be determined by the EYETONE reflectance colorimeter in a fashion similar to that of DEXTROSTIX reagent strips. Alternatively, semiquantitative results can be obtained using the glucose indicator of the present invention by comparing the color produced with a panel of standard colors obtained with known concentrations of glucose employing the same glucose indicator.

The relationship between K (the absorption coefficient of the specimen) and the concentration of the absorbing species (i.e. glucose) is given by the Kubelka-Monk equation which is provided, along with a detailed discussion of reflectance spectrophotometry in Kortumi, G., *Reflectance Spectroscopy*, Springer-Verlag Inc., New York, 1969.

The term K/S, used in the example, is a ratio that is defined by the formula $(1-R)^2/2R$, wherein R is reflectance and S is the scattering coefficient of the particular carrier used. Therefore, K/S is proportional to the amount of chromogen formed by the reaction. Readings in the example were taken at the wavelengths indicated.

Horeseradish peroxidase and glucose oxidase used in the example were obtained from The Research Products Division, Miles Laboratories, Inc., Elkhart, Ind. A copolymer of methyl vinyl ether and maleic anhydride (Gantrez AN-139) and polyvinyl pyrrolidine (PVP) were obtained from GAF Corp., Chemical Products, New York, N.Y.). The solvent used in preparing the solutions can be water, physiological solutions, organic solvents, such as methanol, or mixtures thereof.

The example shown is merely illustrative and is not to be construed as a limitation of the invention. One skilled in the art will be able to make such variations, substitutions and changes in the ingredients and parameters as may seem desirable.

EXAMPLE I

Devices were prepared to incorporate compositions for the quantitative determination of glucose. The compositions used in preparing the devices each had a different concentration of the indicator 3,3',5,5'tetramethylbenzidine (TMB). The effect of this difference on stability over time of the color formed was examined.

A first impregnating solution was prepared to contain the following:

| Components | Quantity | Final Concentration |
|---|---|---|
| ethanol | 25 milliliter (ml) | 25% volume/volume (v/v) |
| H$_2$O | 40.5 ml | |
| glucose oxidase (5 × 10$^3$ IU/ml) | 1.6 ml | 8 × 10$^4$ IU/liter |
| horseradish peroxidase (90.8 IU/mg) | 250 milligrams (mg) | 22 × 10$^5$ IU/liter |
| citrate buffer (1.8 M; pH 4.8) | 25 ml | 0.36 Molar (M) |
| Gantrez AN-139 in H$_2$O (10% w/v) | 12 ml | 1.2% weight/volume (w/v) |
| PVP | 300 mg | 3% (w/v) |

A second impregnating solution was prepared for each of the TMB concentrations to be tested by adding 10, 25, 50 and 75 grams of TMB, respectively, to four 1.0 liter solutions of chloroform containing 17.5 grams of ethyl cellulose each. The final concentration of TMB in these impregnating solutions was 41.9, 104, 208 and 312 millimolar (mM), respectively, and the formulae of these solutions are designated as I, II, III and IV. Thus, the relationships of the millimolar quantities of TMB in impregnating solutions I to IV to the number of International Units of glucose oxidase in the first impregnating solution are 0.52, 1.30, 2.60 and 3.90 mM per 1000 I.U., respectively. Similarly, the relationships of the weight of TMB in impregnating solutions I to IV to the number of International Units of glucose oxidase in the first impregnating solution are 0.125, 0.313, 0.625, and 0.938 gm/1000 I.U., respectively. All of these relationships are shown on Table I for the respective impregnating solutions I to IV.

Four sheets of Eaton-Dikeman 204 (E & D) filter paper were impregnated to saturation with the first impregnating solution and dried at 80° C. Each of the so-impregnated sheets was then impregnated to saturation in a separate one of the second impregnating solutions and dried at 60° C.

The papers so prepared were cut to 0.5 centimeter (cm)×1.0 cm to form test devices. The devices were then backed with double-faced adhesive tape and fixed thereby to organoplastic support members. Each device prepared contained approximately 1.7 I.U. of glucose oxidase, and 5.4 I.U. of peroxidase. The final amounts of TMB in the devices containing formulations I-IV were approximately 0.22, 0.55, 1.10 and 1.6 mg, respectively.

Devices of each formulation were tested by contacting them respectively with a separate one of each of four aqueous glucose solutions. The glucose concentrations in these solutions were 93, 201.9, 302.4 and 372.2 milligrams/deciliter (mg/dl) respectively. After saturation of the carrier of each device with sample the reaction was allowed to proceed for 60 seconds. Any excess sample on the device was then washed off by momentarily placing the device in a stream of running water and blotting away excess liquid using ordinary facial tissue. The device was then placed in a recording reflectance spectrophotometer and the color change was read at 550 nanometers (nm) 20 seconds and again at 60 seconds after washing. The reflectance values observed were converted to K/S values as previously described and the results obtained are shown in Table I.

TABLE I

| Glucose Level | K/S | |
|---|---|---|
| (mg/dl) | 20 sec. | 60 sec. |
| Formula I | | |
| 0.52 mM (0.125g) TMB per 1000 I.U. of glucose oxidase (GOD) | | |
| 93 | 0.219 | 0.215 |
| 201.9 | 0.677 | 0.558 |
| 302.4 | 1.460 | 1.000 |
| 372.2 | 1.710 | 1.150 |
| Formula II | | |
| 1.30 mM (0.313g) TMB per 1000 I.U. GOD | | |
| 93 | 0.238 | 0.239 |
| 201.9 | 0.651 | 0.640 |
| 302.4 | 1.200 | 1.100 |
| 372.2 | 1.560 | 1.310 |
| Formula III | | |
| 2.60 mM (0.625g) TMB per 1000 I.U. GOD | | |
| 93 | 0.278 | 0.283 |

TABLE I-continued

| Glucose Level | K/S | |
|---|---|---|
| (mg/dl) | 20 sec. | 60 sec. |
| 201.9 | 0.630 | 0.634 |
| 302.4 | 1.170 | 1.160 |
| 372.2 | 1.550 | 1.530 |
| Formula IV | | |
| 3.90 mM (0.938g) TMB per 1000 I.U. GOD | | |
| 93 | 0.279 | 0.281 |
| 201.9 | 0.716 | 0.715 |
| 302.4 | 1.280 | 1.210 |
| 372.2 | 1.480 | 1.430 |

Figure 5:
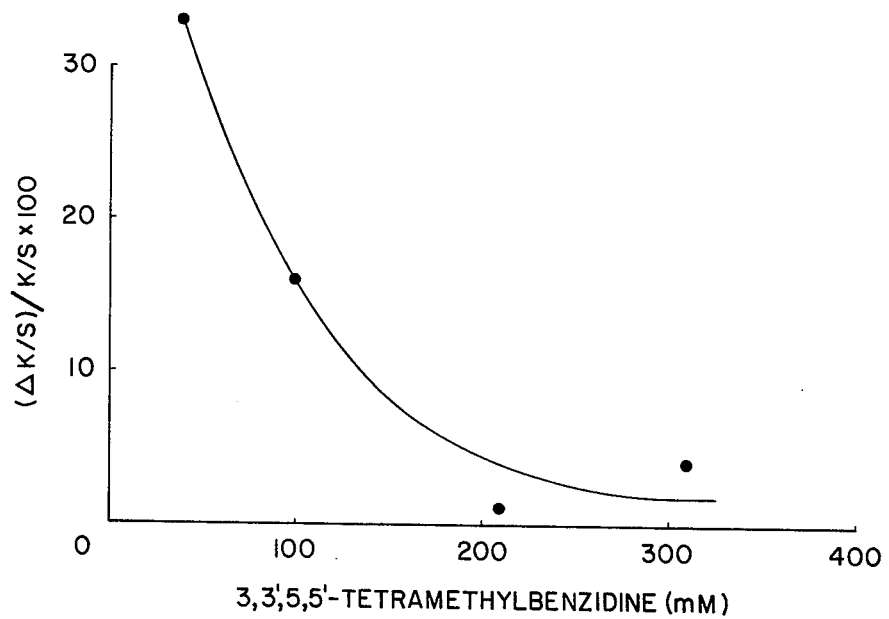
FIG. 5 is a graphical representation of the percentage of change in color observed, defined as $(\Delta K/S)/K/S \times 100$, for the test devices used to obtain the data illustrated in FIGS. 1-4.

FIGS. 1-4 graphically represent the data reported in Table I for devices containing formulations I-IV, respectively. The solid lines represent the K/S readings taken at 20 seconds after washing of the device and the broken lines represent the K/S readings at 60 seconds. FIG. 5 graphically represents the percentage of change in color observed. defined as $(\Delta K/S)/K/S \times 100$), for devices containing each of the formulations I-IV.

A stable color (blue) was visually observed substantially immediately upon removing the excess sample from the devices having formulations III and IV, whereas degradation of color, with resultant error in glucose levels detected, occured with the devices having formulations I and II. The devices with formulations III and IV, having higher TMB concentrations, give a substantially immediate color end point which is stable thereafter.

Figure 2:
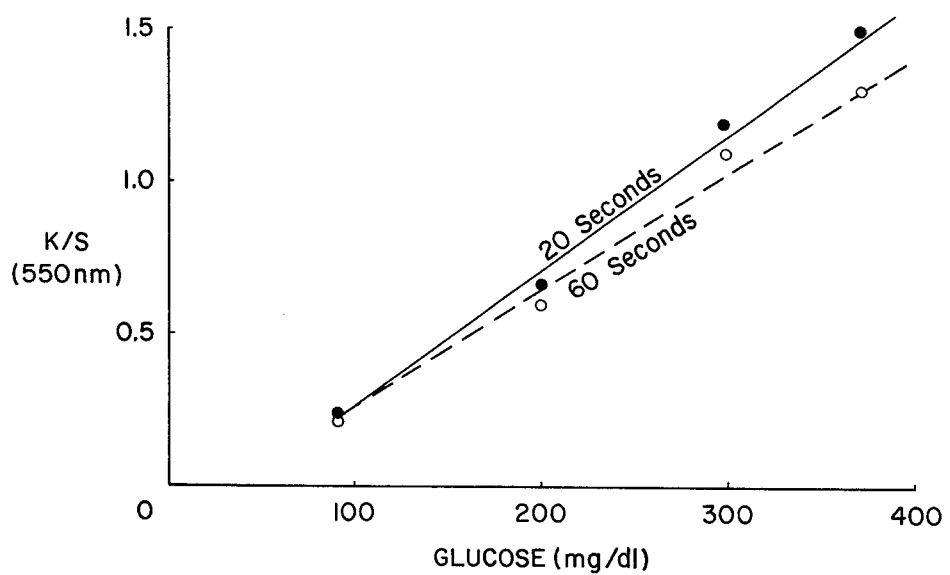
FIG. 2 is a graphical representation of the data reported in Table I using glucose test devices produced with the use of impregnating solution formula II of Example I, such representation being obtained by plotting K/S vs glucose concentration.
Figure 3:
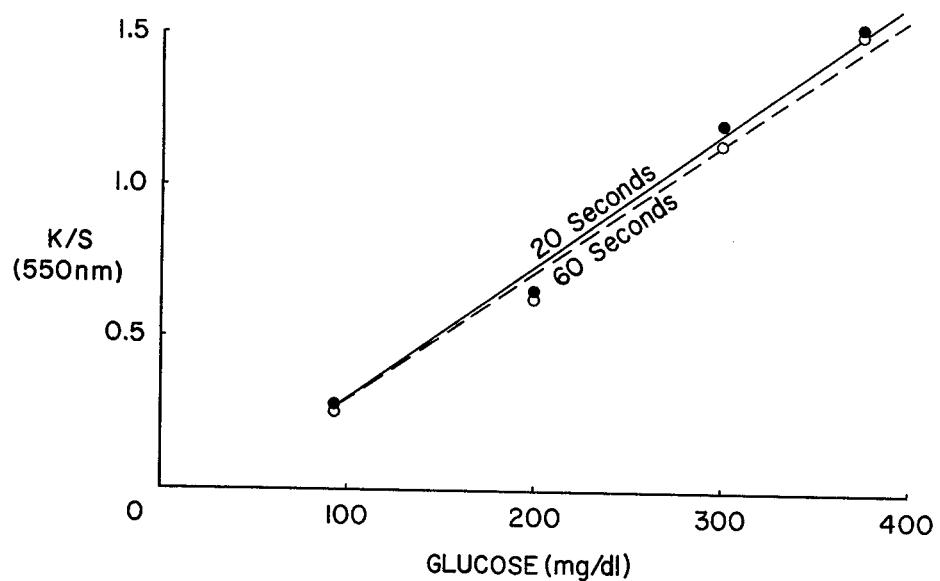
FIG. 3 is a graphical representation of the data reported in Table I using glucose test devices produced with the use of impregnating solution formula III of Example I, such representation being obtained by plotting K/S vs glucose concentration.
Figure 4:
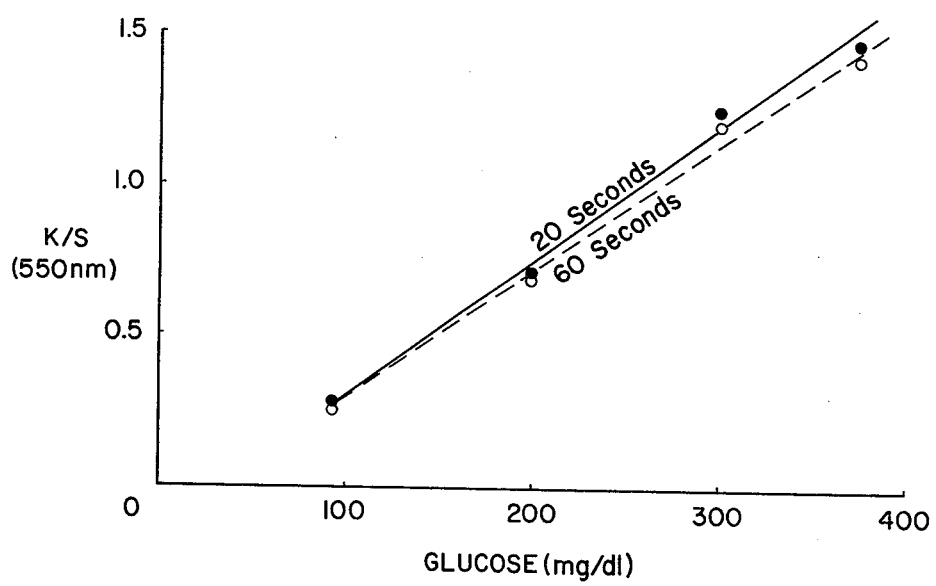
FIG. 4 is a graphical representation of the data reported in Table I using glucose test devices produced with the use of impregnating solution formula IV of Example I, such representation being obtained by plotting K/S vs. glucose concentration.

FIGS. 1 and 2 show that there is a substantial change between the readings taken at 20 seconds and at 60 seconds. These readings are proportional to the amount of chromogen formed. The amount of glucose reported by such devices is therefore totally unreliable. In contrast, the virtually identical readings shown in FIGS. 3 and 4 demonstrate the stability of the color formed in accordance with the invention. FIG. 5 shows a percentage of color change from the 20 second reading to the 60 second reading of over 30% using formulation I and less than 3% using formulation III. The present invention therefore provides a greater than 10-fold improvement over the prior art.

Although the invention has been described with a certain degree of particularity, it is understood that the present disclosure has been made only by way of example and that numerous changes in the details may be resorted to without departing from the scope of the invention.

What is claimed is:

1. A composition for the determination of glucose in a body fluid sample which comprises glucose oxidase, peroxidase, a buffer effective to maintain a pH of from about 4 to about 7.5, a stabilizing agent and 3,3',5,5'-tetramethylbenzidine, wherein the 3,3',5,5'tetramethylbenzidine is present in a concentration of at least about 2.6 millimoles per thousand International Units of glucose oxidase activity.

* * * * *